US005452726A

United States Patent [19]
Burmeister et al.

[11] Patent Number: 5,452,726
[45] Date of Patent: Sep. 26, 1995

[54] INTRAVASCULAR GUIDE WIRE AND METHOD FOR MANUFACTURE THEREOF

[75] Inventors: Paul H. Burmeister, White Bear Lake; Richard E. Cappetta, Plymouth; Steven S. Hackett, Minnetonka; Paul Slaikeu, Vadnais Heights, all of Minn.

[73] Assignee: SciMed Life Systems, Inc., Minneapolis, Minn.

[21] Appl. No.: 319,772

[22] Filed: Oct. 7, 1994

Related U.S. Application Data

[63] Continuation of Ser. No. 34,174, Mar. 12, 1993, abandoned, which is a continuation of Ser. No. 716,678, Jun. 18, 1991, abandoned.

[51] Int. Cl.⁶ .................................................. A61B 5/00
[52] U.S. Cl. ........................ 128/772; 128/657; 604/281
[58] Field of Search ........................... 128/772, 657; 604/95, 164, 280, 281, 282

[56] References Cited

U.S. PATENT DOCUMENTS

| | | | |
|---|---|---|---|
| 4,282,876 | 8/1981 | Flynn | 128/349 |
| 4,345,602 | 8/1982 | Yoshimura et al. | 128/349 |
| 4,456,017 | 6/1984 | Miles | 128/772 |
| 4,534,363 | 8/1985 | Gold | 128/772 |
| 4,682,607 | 7/1987 | Vaillancourt et al. | 128/772 |
| 4,721,117 | 1/1988 | Mar et al. | 128/772 |
| 4,729,914 | 3/1988 | Kliment et al. | 428/36 |
| 4,739,768 | 4/1988 | Engelson | 128/658 |
| 4,811,743 | 3/1989 | Stevens | 128/772 |
| 4,835,003 | 5/1989 | Becker et al. | 427/2 |
| 4,841,976 | 6/1989 | Packard et al. | 128/657 |
| 4,867,174 | 9/1989 | Shribiski | 128/772 |
| 4,884,579 | 12/1989 | Engelson | 128/772 |
| 4,899,787 | 2/1990 | Ouichi et al. | 138/131 |
| 4,922,924 | 5/1990 | Gambale et al. | 128/772 |
| 4,925,445 | 5/1990 | Sakamoto et al. | 604/95 |
| 4,955,862 | 9/1990 | Sepetka | 604/164 |
| 4,961,731 | 10/1990 | Bodicky et al. | 604/264 |
| 4,977,901 | 12/1990 | Ofstead | 128/772 |
| 4,991,602 | 2/1991 | Amplatz et al. | 128/772 |
| 5,069,226 | 12/1991 | Yamauchi et al. | 128/772 |
| 5,078,702 | 1/1992 | Pomeranz | 604/280 |
| 5,095,915 | 3/1992 | Engelson | 128/772 |
| 5,129,890 | 7/1992 | Bates et al. | 604/281 |

FOREIGN PATENT DOCUMENTS

| | | |
|---|---|---|
| 0340304 | 8/1989 | European Pat. Off. . |
| 0340304 | 11/1989 | European Pat. Off. . |
| 0380102 | 8/1990 | European Pat. Off. . |
| 0395098 | 10/1990 | European Pat. Off. . |
| 0405823 | 1/1991 | European Pat. Off. . |
| 0407965 | 1/1991 | European Pat. Off. . |
| 2401-668 | 8/1977 | France . |

(List continued on next page.)

OTHER PUBLICATIONS

*Current Problems In Diagnostic Radiology;* Charles J. Tegtmeyer, M.D.; Mar./Apr. 1987.

*Primary Examiner*—Stephen C. Pellegrino
*Assistant Examiner*—Guy V. Tucker
*Attorney, Agent, or Firm*—Nawrocki, Rooney & Sivertson

[57] ABSTRACT

A guide wire, and a method for the manufacture thereof, having a core and a plastic jacket enclosing the core. The plastic jacket comprises a proximal portion formed of a first plastic material and a distal jacket portion formed of a second plastic material. The distal end of the proximal jacket portion and the proximal end of the distal jacket portion substantially abut each other and are of substantially equal outer diameters so as to form a smooth transition between the proximal and the distal jacket portions. According to another aspect, there is provided a guide wire with a selectively formable metallic core and a plastic jacket encasing the formable core. The plastic jacket has a distal portion with a hydrophilic coating and a proximal portion without a hydrophilic coating. According to another aspect, there is provided a guide wire having a formable metallic core and a plastic jacket encasing the formable core. The plastic jacket has a distal portion that is more radiopaque than a proximal portion.

23 Claims, 1 Drawing Sheet

FOREIGN PATENT DOCUMENTS

| | | |
|---|---|---|
| 60-012069 | 1/1985 | Japan . |
| 2180277 | 7/1990 | Japan ..................................... 128/772 |
| PCT85/01444 | 4/1985 | WIPO . |
| PCT/WO91/00051 | 8/1989 | WIPO . |
| 8909626 | 10/1989 | WIPO ..................................... 604/280 |

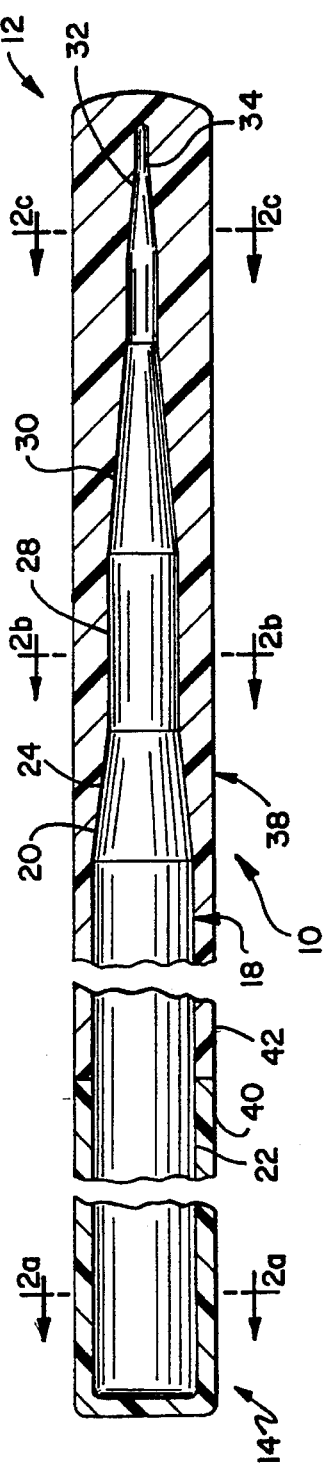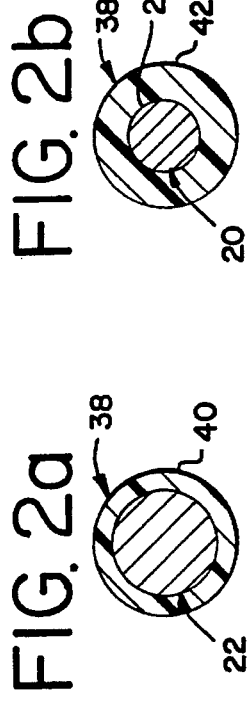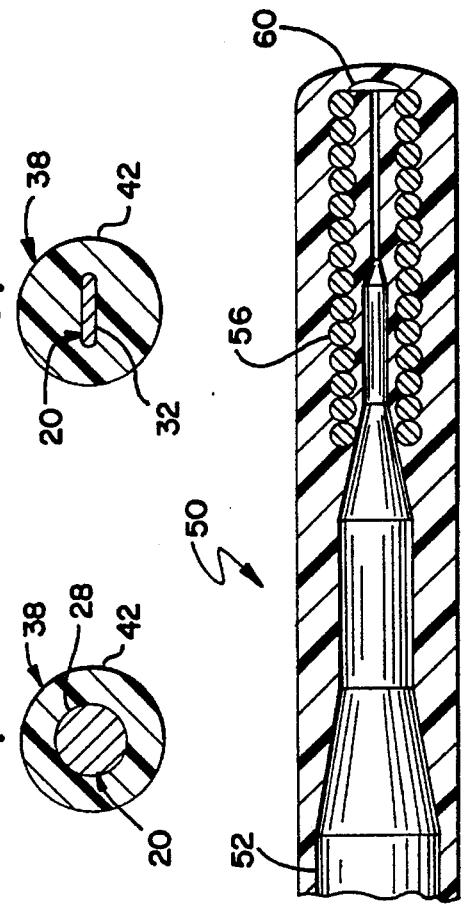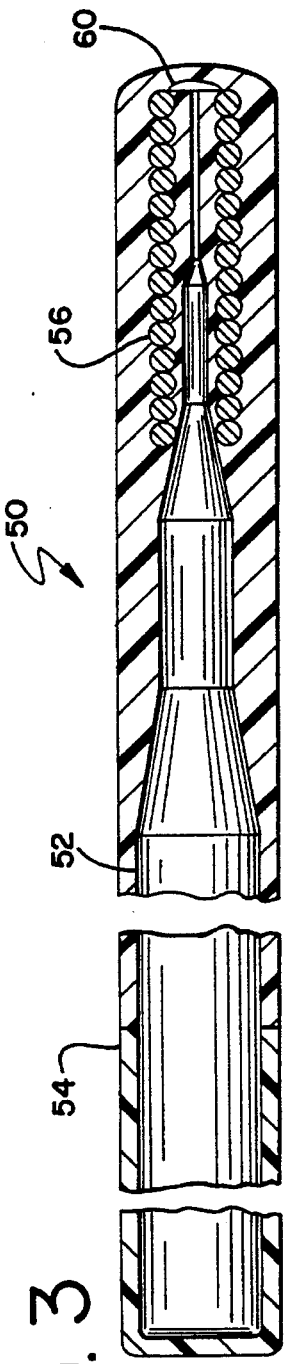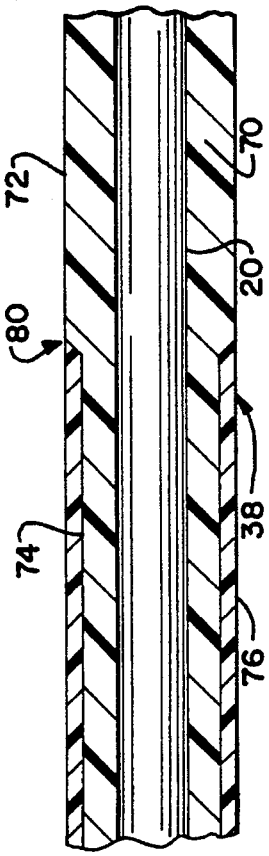

INTRAVASCULAR GUIDE WIRE AND METHOD FOR MANUFACTURE THEREOF

REFERENCES TO CO-PENDING APPLICATIONS

This application is a continuation of U.S. Ser. No. 08/034,174, filed Mar. 12, 1993, entitled "Intravascular Guide Wire and Method for Manufacture Thereof", now abandoned, which is a continuation of U.S. Ser. No. 07/716,678, filed Jun. 18, 1991, entitled "Intravascular Guide Wire and Method for Manufacture Thereof" now abandoned.

BACKGROUND OF THE INVENTION

The present invention relates to intravascular guide wires, and methods of manufacture thereof. In particular, the present invention relates to an intravascular guide wire, and methods for the manufacture thereof, with improved properties to enhance the use thereof.

Guide wires are used in various procedures in both the coronary regions and the peripheral regions of the body. Various sizes and lengths of guide wires are made to be suitable for various uses and locations in the body. For example, guide wires of a very small diameter, on the order of 0.010 to 0.018 inches may be suitable for use in narrow coronary vessels. Such guide wires may have an extremely floppy tip distal tip which may be bent or preformed by the physician to facilitate placement of the guide wire at the desired location. Other guide wires have larger diameter, for example 0.035 inches. These larger diameter guide wires may be especially useful in peripheral regions of the body. Larger diameter guide wires may be provided with very flexible tips or with relatively rigid tips depending upon the particular needs of the patient and the preferences of the physician. Guide wires come in a range of sizes in addition to those discussed above.

Some of the characteristics preferred in guide wires by some physicians include strength, the ability to provide a track for a balloon or other device to advance over, and good torsional transmittance. A discussion of these and other preferred characteristics of guide wires is in *Endovascular Surgery*, by Moore, W. S. and Ahn, S. S; p. 157, W.B. Saunders Co. (1989). One of the characteristics considered desirable by some physicians in a guide wire is that it should be easy to grip and use manually at the proximal portion.

Accordingly, it is an object of the present invention to provide a guide wire with favorable characteristics.

SUMMARY OF THE INVENTION

According to a first aspect of the invention, there is provided a guide wire, and a method for the manufacture thereof, having a core and a plastic jacket enclosing the core. The plastic jacket comprises a proximal portion formed of a first plastic material and a distal jacket portion formed of a second plastic material. The distal end of the proximal jacket portion and the proximal end of the distal Jacket portion are of substantially equal outer diameters so as to form a smooth transition between the proximal and the distal jacket portions.

According to another aspect of the invention, there is provided a guide wire, and a method for the manufacture thereof, with a core that is selectively formable in at least a distal portion thereof, and a plastic jacket encasing the selectively formable core. The plastic Jacket has a distal portion with a hydrophilic coating and a proximal portion without a hydrophilic coating.

According to another aspect of the invention, there is provided a guide wire, and a method for the manufacture thereof, having a core that is selectively formable, at least in a distal portion thereof, and a plastic jacket encasing the core. The plastic jacket has a distal portion that is more radiopaque than a proximal portion.

BRIEF DESCRIPTION OF THE DRAWINGS

FIG. 1 is a sectional view of a first embodiment of the present invention.

FIG. 2a shows a cross section of the embodiment of FIG. 1 along line 2a–2a'.

FIG. 2b shows a cross section of the embodiment of FIG. 1 along line 2b–2b'.

FIG. 2c shows a cross section of the embodiment of FIG. 1 along line 2c–2c'.

FIG. 3 is a sectional view of another embodiment of the present invention.

FIG. 4 a sectional view of yet another embodiment of the present invention.

DETAILED DESCRIPTION OF THE PRESENTLY PREFERRED EMBODIMENTS

Referring to FIG. 1 there is depicted a first preferred embodiment of the present invention. This embodiment is an intravascular guide wire 10. This guide wire 10 has a distal end 12 and a proximal end 14. The guide wire 10 may be approximately 180 centimeters in length and have an outside diameter of approximately 0.035 inches. Other lengths and diameters may be provided so that a range of sizes of guide wires may be available suitable for the different needs of various individual patients and the preferences of physicians. Such other sizes are contemplated within the scope of the present invention and of this embodiment in particular.

The guide wire 10 includes a core 18. The core may be made of a strong, yet flexible material, such as a metal, like stainless steel or nitinol, or other materials, or combinations thereof. In a preferred embodiment, the core 18 is made at least in part of a selectively formable metallic material, as explained in more detail below. The core 18 extends from the distal end 12 to the proximal end 14 of the guide wire 10.

In a preferred embodiment, the core 18 includes a distal portion 20 and a proximal portion 22. The proximal and distal portions are preferably formed of a single metallic wire. The distal portion 20 has a smaller cross section than the proximal portion 22 to impart greater flexibility to the distal end of the guide wire. In a preferred embodiment, the distal portion 20 of the guide wire comprises a series of stages or regions of tapered portions and portions of uniform cross section, as explained in more detail below. The series of stages of tapered portions and portions of uniform cross section are intended to impart increasing levels of flexibility to the guide wire toward the distal end.

In this embodiment, the proximal portion 22 of the core 18 has a diameter of approximately 0.018 inches. FIG. 2a shows a cross section of the guide wire in the proximal portion 22. The proximal portion 22 of the core 18 extends from a proximal end of the guide wire 10 to a proximal end of the distal portion 20 of the core 18. In this embodiment, the distal portion 20 of the core 18 is approximately 10.50 inches in length.

The distal portion 20 of the core includes a first region 24 immediately adjacent to and distal of the proximal portion 22. This first region 24 of the distal portion 20 of the core is approximately 2.0 inches in length. In the first region 24, the core 18 tapers from the diameter of the proximal portion 20 (e.g. 0.018 inches) to a diameter of approximately 0.009 inches. In this first region 24, the core has a circular cross section.

The distal portion 20 of the core next includes a second region 28 immediately adjacent to and distal of the first region 24. This second region 28 of the distal portion 20 of the core is approximately 4.0 inches in length. FIG. 2b shows a cross section of the guide wire in this region. The second region 28 is a region of approximately uniform cross section. In this second region 28, the core also preferably has a circular cross section.

The distal portion 20 of the core next includes a third region 30 immediately adjacent to and distal of the second region 28. This third region 30 of the distal portion 20 of the core is approximately 2.0 inches in length. In the third region 30, the core 18 tapers from the diameter of the second region 28 (e.g. 0.0090 inches) to a diameter of approximately 0.00525 inches. In this third region 30, the core also has a circular cross section.

The distal portion 20 of the core next includes a fourth region 32 immediately adjacent to and distal of the third region 30. This fourth region 32 of the distal portion 20 of the core is approximately 1.75 inches in length. In the fourth region 32, the core 18 is flattened toward a distal end 34 thereof to form a ribbon shape having dimensions of approximately 0.010 by 0.00225 inches. FIG. 2c shows a cross section of the guide wire in this region. The ribbon shape of this region causes the guide wire to tend to flex in one plane thereby facilitating the use thereof. In the fourth region 32, the length of the distal flattened portion is approximately 0.5 inches, the length of the portion of circular cross section is approximately 0.7 inches, and a transition zone between these portions has a length of approximately 0.7 inches.

The distal portion 20 of the core wire, including the various regions of tapered and uniform cross section, may be formed by methods known in the art, such as chemical washes, polishes, grinding, or compressing.

The guide wire 10 also includes a plastic jacket 38 extending from the proximal end 14 to the distal end 12. In a first preferred embodiment, the plastic jacket 38 is formed of a proximal jacket portion 40 and a distal jacket portion 42. The outside diameter of the plastic jacket 38 in this embodiment is approximately 0.035 inches although other diameters may be provided for guide wires of other dimensions.

The distal jacket portion 42 is approximately 18 inches in length and extends proximally from the distal end of the guide wire 10. The distal end of the distal jacket portion 42 extends over and covers the distal end of the core wire 18. The proximal jacket portion 40 extends from the proximal end of the guide wire 10 distally. In this embodiment, the proximal end of the distal jacket portion 42 substantially abuts the distal end of the proximal jacket portion 40. At the location at which the proximal and distal jacket portions abut, the outside diameters of the jacket portions are substantially the same and form a smooth transition at that location so that the guide wire can be readily inserted into and moved within a catheter or vessel or that a catheter or other device can be readily advanced over the guide wire.

These two jacket portions are provided to yield features related to functions specifically associated with their respective locations. In this embodiment, the proximal jacket portion 40 is made of a Teflon i.e. polyedrafluoroethylene material and the distal jacket portion 42 is made of polyurethane. Alternatively, the proximal jacket portion 40 may be made of another material or combination of materials, such as flouroresins, such as Kynar ($CH_2CF_2$), high density polyethylene, Delrin (polyacetal), Hytrel or polypropylene. The distal jacket portion 42 may be made of other polymers or copolymers, or elastomers, or fluoroelastomers or silicone, Hytrel or nylon.

In a preferred embodiment, the distal jacket portion has a hydrophilic coating applied to it to make the surface highly lubricious when it comes in contact with a fluid such as blood. The hydrophilic coating is believed to improve the biocompatability of the guide wire. This is based in part on observations that hydrophilic surfaces are generally less thrombogenic, and more specifically, tend to exhibit reduced platelet activation and aggregation compared to hydrophobic surfaces. In a preferred embodiment, the composition of the coating is a mixture of a hydrogel and a polyurethane in an organic/water solvent mixture. The solution mixture is applied to the distal jacket portion 42 and dried. In a preferred embodiment, polyvinyl pyrrolidone (PVP) is used as the hydrogel and commercial polyurethanes such as Dow (Pellethane 2363 Series) or Thermedics (the Tecophane or Tecoflex families) may be used. A polymer blend having an affinity to the polyurethane substrate of the distal jacket portion (via the urethane and the solution) is used while the other component is a slippery otherwise water-soluble material. The hydrogel will not tend to dissolve away because it is ensnared with the water insoluble polyurethane.

As an alternative to using a hydrophilic coating, a different coating may be applied to the guide wire jacket to enhance its lubriciousness. Such a coating may be a silicone coating or other lubricious material.

In a preferred embodiment, the hydrophilic coating is applied only to a distal portion of the guide wire, and in particular, only to the distal jacket portion 42. This is facilitated because the preferred hydrophilic coating is formulated to adhere to the urethane material of the distal jacket portion but not adhere to many different materials including the preferred material of the proximal jacket.

As mentioned above, the proximal jacket portion is made of Teflon I.e, polyetrafluoroethylene which also provides a low friction surface though not as low friction as that of the distal jacket portion with the hydrophilic coating applied. It is advantageous for the proximal portion of the guide wire have a low friction surface in order to traverse a catheter lumen or a vessel. However, because the proximal portion of the guide wire will likely be in a portion of the vasculature not as tortuous as the distal portion, it would not require a surface of as high lubricity as the distal portion and therefore Teflon i.e., polyetraflufroethylene is a good choice of materials.

Moreover, this combination of low friction surfaces has the additional advantage that a very low friction surface, such as one having a hydrophilic coating, is used only on the distal portion of the guide wire. A very low friction surface, such as one having a hydrophilic coating, would be so slippery that it would be difficult for a physician to handle if it were on the proximal end as well. Accordingly, at the proximal end of the guide wire, this embodiment includes a surface that is easy for the physician who would be manipulating the guide wire from the proximal end to handle and yet is of sufficiently low friction so that it can readily traverse portions of the patient's vessels and provide good guide wire movement in a catheter.

It is also preferred that the distal portion of the guide wire be provided with enhanced radiopaque properties. In the preferred embodiment, this is done by loading the material from which the distal jacket 42 is made with radiopaque materials such as barium, bismuth or tungsten. The loading of the distal jacket of polyurethane with a radiopaque material enhances the ability of a physician to observe the position of the distal end of the guide wire in the body of the patient by means of fluoroscopy.

In a preferred embodiment, the proximal jacket portion 40 of Teflon i.e., polyetrofluorothylene is heat shrunk onto the core wire. The distal jacket portion 42 is installed over the core wire by heating a sleeve of polyurethane to a temperature until it is reformed around the core wire. The proximal and distal jackets may be finished by a centerless grinding method so that the transition between the jacket portions is smooth.

In a further embodiment, the guide wire has a core that is selectively formable at least in a distal portion thereof. By a selectively formable core, it is meant that the wire from which the core is made may be bent to a particular shape and that the shape will be maintained by the wire. This allows the physician to impart a particular shape to the guide wire, by bending or kinking it for example, to facilitate its placement into a patient's vasculature. To provide this selective formability, in a preferred embodiment, the entire core wire may be made of stainless steel. Other materials may be used to provide this feature. The use of a formable material, such as stainless steel, provides advantages in the guide wire over materials that cannot be formed, such as superelastic materials like nitinol. Superelastic materials, like nitinol, are so resilient that they tend to spring back to their original shape even if bent, thus are not formable. Although superelastic material may be provided with a "preformed" memory shape, such a preformed shape is typically determined in the manufacture of the guide wire and cannot readily be altered or modified by the physician by simply bending the guide wire prior to use. Although use of superelastic materials such as nitinol in guide wire applications may provide some advantages in certain uses, a formable core, such as of stainless steel, which can be formed by the physician to a shape suitable for a particular patient or preferred by that physician, provides an advantage that cannot be obtained with a superelastic core guide wire.

In a further preferred embodiment, the guide wire may include a core wire of a material having formable properties at a distal portion thereof and non-formable (e.g. superelastic properties) proximally. Such a construction would provide advantages in certain guide wire usages. A guide wire having these properties could be formed by using a superelastic material such as nitinol for the core wire and reducing its superelasticity in a distal portion thereof. This may be effected by heating the distal end of the superelastic core wire. Another means to reduce the superelastic properties of a distal end of the core wire would be to shape it mechanically, e.g. flattening it. Other methods of reducing the superelastic properties of the core wire may also be used. With a core wire having this dual combination of a formable distal portion and a superelastic proximal portion, desired shapes could be imparted by a physician to the distal end of the guide wire to facilitate making turns, etc., in tortuous vessel passages, while in the same guide wire the more proximal portion would possess superelastic properties to allow it to follow the distal portion through the tortuous passages without permanently deforming. This combination of formable and non-formable properties in the core wire may also be provided by using more than one material for the core wire or more than one wire.

FIG. 3 shows another preferred embodiment of the present invention. This embodiment of the guide wire is similar in some respects to the embodiment of the guide wire, described above. Although this embodiment of the guide wire may be provided in large sizes (e.g. 0.035 inches), this embodiment is especially suitable for a guide wire of a smaller diameter, e.g. having an outer diameter of approximately 0.018 inches. If provided in a guide wire of smaller diameter, the diameter of the core wire and plastic jacket would be correspondingly smaller. Like the embodiment described above, this guide wire includes a core 52 surrounded by a plastic jacket 54. The core 52 is preferably of a selectively formable material, as described above. In addition, in this embodiment, a marker 56 is provided at a distal end 58 of the guide wire 50. This marker 56 is located around the distal portion of the core wire 52 underneath the plastic jacket 54. In this embodiment, the marker 56 is a coil spring. Alternatively, the marker may be a ribbon, another wire, or any other similar component. A tip 60 may be provided at the distal end of the core wire 52 to facilitate placement and connection of the marker 56.

The marker 56 may be made of platinum or stainless steel or other material. The marker 56 may be provided with radiopaque properties by selecting a material such as platinum. This may be in addition or as an alternative to providing radiopaque properties in the jacket portion through the use of loading with radiopaque materials. The use of a radiopaque marker may be preferred in smaller diameter guide wires where the plastic jacket, even if loaded with a radiopaque material, is of such a small size that it could be difficult to discern under fluoroscopy.

FIG. 4 shows another preferred embodiment of the present invention. In the embodiment in FIG. 4, a core wire 20 extends from a distal to a proximal end of the guide wire. As in the embodiment described above, the core wire 20 is surrounded by a core wire jacket 38. In this embodiment, the core wire jacket 38 is comprised of a first jacket 70. The first jacket 70 of this embodiment is comprised of a first portion 72 and a second portion 74. The core wire jacket 38 also includes a second jacket 76. The second jacket 76 covers the first jacket 70 over the second portion 74 thereof. The second jacket 76 may correspond to the proximal jacket of the previous embodiments. The second jacket 76 may be a thin tubing that is heat shrunk onto the first jacket 70 over a proximal portion thereof. Alternatively, the second jacket 76 may be applied by other methods, such as by spraying, dipping, etc.

In a preferred embodiment, the outer diameter of the second jacket 76 when it is in position surrounding the first jacket 70 is approximately the same as the outer diameter of the first jacket 70 in the first portion 72 thereof at least in an area 80 of the guide wire where the second jacket 76 ends so that the overall diameter of the guide wire through this area 80 is substantially uniform. This uniformity may be further enhanced by polishing, grinding, or other means. To further provide for this uniformity in diameter, the second portion 74 of the first jacket 70 may be provided with a diameter that is less than that of the first portion 72 of the first jacket 70. This reduction in diameter may be formed by grinding, stretching, chemical erosion, or other means.

In a preferred embodiment, the second jacket 76 covers the proximal portion of the guide wire and an exposed first portion 72 of the first jacket 70 extends to a distal end of the guide wire. The first jacket 70 and second jacket 76 may be provided with properties specifically directed to their respective functions, as explained above in regard to the embodiment of the guide wire in which the jackets are in an abutting relationship. For example, the first jacket 70 may be made of polyurethane and the second jacket 76 may be made of a Teflon-like, i.e., polyethrofluoroethylene material. A hydrophilic coating may be applied to the first jacket 70 in the first portion 72 thereof to enhance lubricity, as explained above. If this embodiment of the guide wire is intended for use in peripheral regions of the body, it may have an outside diameter of approximately 0.035 inches. Other dimensions may be suitable as well for other size guide wires. As in the previously described embodiments, the core 20 may be a material such as stainless steel or nitinol and may have formable properties in at least a portion thereof.

It is intended that the foregoing detailed description be regarded as illustrated rather than limiting and that it is understood that the following claims including all equivalents are intended to define the scope of the invention.

We claim:

1. A guide wire comprising:

an elongated core having a length and a width, said elongated core further having an axial surface extending the length of said elongated core and a proximal end surface and a distal end surface, and a plastic jacket extending around said axial surface of said elongated core, said plastic jacket comprising:

a proximal jacket portion formed of a first plastic material, said proximal jacket portion extending around at least a portion of said axial surface of said elongated core, and a distal jacket portion formed of a second plastic material different from the first plastic material, said distal jacket portion extending around at least a portion of said axial surface of said elongated core, wherein the distal end of said proximal jacket portion and the proximal end of said distal jacket portion forming a transition between said proximal and said distal jacket portions wherein the distal jacket portion further includes a surface coating that is substantially more lubricous than said proximal jacket portion when exposed to water-based liquid.

2. The guide wire of claim 1 wherein said distal jacket portion is made of polyurethane.

3. The guide wire of claim 1 wherein said proximal jacket portion is made of polytetrafluoroethylene material.

4. The guide wire of claim 1 wherein said distal jacket portion has radiopaque properties.

5. The guide wire of claim 4 wherein said distal jacket portion is loaded with a material selected from a group consisting of bismuth, barium, and tungsten.

6. The guide wire of claim 1 further comprising a radiopaque marker located around a distal end of said core beneath said plastic jacket.

7. The guide wire of claim 6 wherein said marker is substantially radiopaque.

8. A guide wire of claim 1 wherein said distal jacket portion has the hydrophilic coating.

9. The guide wire of claim 1 wherein said core is formable in at least a portion thereof.

10. The guide wire of claim 9 wherein said core is made of stainless steel.

11. The guide wire of claim 9 in which the core is formable in a distal portion thereof and nonformable in a proximal portion thereof.

12. The guide wire of claim 1 wherein said proximal jacket portion includes a surface that does not become substantially more lubricous when exposed to water based liquid.

13. The guide wire of claim 1 wherein said distal jacket portion has a distal end and a proximal end, said distal end of said distal jacket portion extending over at least a portion of said distal end surface of said elongated core.

14. The guide wire of claim 1 wherein said proximal jacket portion has a distal end and a proximal end, said proximal end of said proximal jacket portion extending over at least a portion of said proximal end surface of said elongated core.

15. A guide wire comprising:

an elongated metallic core formable in at least a portion thereof, said elongated metallic core having a length and a width, said elongated metallic core further having an axial surface extending the length of said elongated metallic core and a proximal end surface and a distal end surface, and a plastic jacket encasing said elongated metallic core, said plastic jacket having a distal portion formed of a first plastic material and a proximal portion formed of a second plastic material different from the first plastic material wherein the distal jacket portion further includes a surface coating that is substantially more lubricous when exposed to a water-based liquid than the proximal jacket portion, said proximal portion of said plastic jacket extending around at least a portion of said axial surface of said elongated core and said distal portion of said plastic jacket extending around at least a portion of said axial surface of said elongated metallic core.

16. The guide wire of claim 15 wherein said core is made of stainless steel.

17. The guide wire of claim 15 wherein said core is tapered at a distal end thereof.

18. The guide wire of claim 15 in which the core is formable in a distal portion thereof and nonformable in a proximal portion thereof.

19. The guide wire of claim 18 in which the core is made of nitinol.

20. A guide wire comprising:

an elongated metallic core formable in at least a portion thereof, said elongated metallic core having a length and a width, said elongated metallic core further having an axial surface extending the length of said elongated metallic core and a proximal end surface and a distal end surface, and a plastic jacket encasing said elongated metallic core, said plastic jacket having a distal portion formed of a first plastic material and a proximal portion formed of a second plastic material said second plastic material being different from said first plastic material, said distal portion being more radiopaque than said proximal portion, and further wherein the distal jacket portion further includes a coating that is substantially more lubricous when exposed to water-based liquid than the proximal jacket portion, said proximal portion and said distal portion of said plastic jacket extending around at least a portion of said axial surface of said elongated metallic core.

21. The guide wire of claim 20 wherein said distal portion is loaded with a material selected from a group consisting of bismuth, barium, and tungsten.

22. The guide wire of claim 21 further comprising a marker located at a distal end of said core beneath said plastic jacket.

23. The guide wire of claim 22 wherein said marker is substantially radiopaque.

* * * * *